United States Patent
Diem et al.

(10) Patent No.: US 8,064,990 B2
(45) Date of Patent: Nov. 22, 2011

(54) ECG ANALYZING DEVICE

(75) Inventors: Björn Henrik Diem, Berlin (DE); Alexander Kraus, Berlin (DE); Oleg Anosov, Erlangen (DE)

(73) Assignee: Biotronik CRM Patent AG (CH)

( * ) Notice: Subject to any disclaimer, the term of this patent is extended or adjusted under 35 U.S.C. 154(b) by 282 days.

(21) Appl. No.: 12/434,754

(22) Filed: May 4, 2009

(65) Prior Publication Data
US 2009/0292218 A1    Nov. 26, 2009

(30) Foreign Application Priority Data
May 20, 2008   (DE) .................. 10 2008 024 453

(51) Int. Cl.
*A61B 5/04*   (2006.01)
(52) U.S. Cl. ...................................... 600/509
(58) Field of Classification Search ............ 607/14, 607/30, 31; 600/300, 523, 509; 128/901
See application file for complete search history.

(56) References Cited

U.S. PATENT DOCUMENTS

| | | | |
|---|---|---|---|
| 6,589,187 B1 | 7/2003 | Dirnberger et al. | |
| 6,731,985 B2 | 5/2004 | Poore et al. | |
| 7,155,275 B2 * | 12/2006 | Linder et al. | 600/509 |
| 7,289,844 B2 | 10/2007 | Misczynski et al. | |
| 2003/0023176 A1 * | 1/2003 | Yonce et al. | 600/510 |
| 2005/0038350 A1 | 2/2005 | Kamath et al. | |
| 2007/0093720 A1 | 4/2007 | Fischell et al. | |
| 2007/0260149 A1 * | 11/2007 | Woellenstein et al. | 600/509 |
| 2008/0004539 A1 | 1/2008 | Ross | |

FOREIGN PATENT DOCUMENTS

EP     13 02 217 A2     4/2003
WO   WO 2007131064 A2   11/2007

OTHER PUBLICATIONS

European Search Report, EP 09 15 8446, Aug. 31, 2009.

* cited by examiner

*Primary Examiner* — George Manuel
*Assistant Examiner* — Robert Wieland
(74) *Attorney, Agent, or Firm* — Craig A. Fieschko, Esq.; DeWitt Ross & Stevens S.C.

(57) ABSTRACT

A device (10) for processing electrocardiogram signals and marker signals includes an input interface (30) for receiving electrocardiogram signals and marker signals detected by an implantable medical device; an analyzer unit (32) connected to the input interface (30) for processing the electrocardiogram signals and marker signals, and an output interface (34) connected to the analyzer unit (32) for output of data representing an analytical report to a playback unit. The analyzer unit (32) is designed to analyze electrocardiogram signals and marker signals in combination, such that the analyzer unit (32) detects relevant particular features on the basis of predefined criteria; assigns a priority to a detected particular feature; and generates an analytical report containing at least a listing of the detected particular features.

30 Claims, 8 Drawing Sheets

Priority:

| High |

Text:

| Detection of irregular noise in RV channel
→ Suspected electrode breakage |

IEGM-presentation:

Recommendation:

| Performing stimulus threshold, sensing and impedance measurements of the RV electrode, optionally with provocation |

Priority:

| High |

Text:

| Indequate VT-2 detection at T-Wave-Oversense in RV channel |

IEGM-presentation:

Recommendation:

| If VF detection is ensured, activation of anti-T-wave oversense option according to Pace |

Priority:

| | Moderate |
|---|---|

Text:

| | Far-field sensing after RV stimulation in atrial channel<br>→ This may lead to inadequate mode switch<br>→ This may lead to false positive results in the atrial arrhythmia statistics |
|---|---|

IEGM-presentation:

Recommendation:

| | - Checking the RA probe position<br>- If nessecary expanding the cross channel blanks in the atrium by 30 ms |
|---|---|

Priority:

| Moderate |
|---|

Text:

| Far-field sensing of the atrium in the LV<br>→ With activated LV protection, this may result in inadequate suppression of LV stimulation and thus to a restriction on CRF therapy |
|---|

IEGM-presentation:

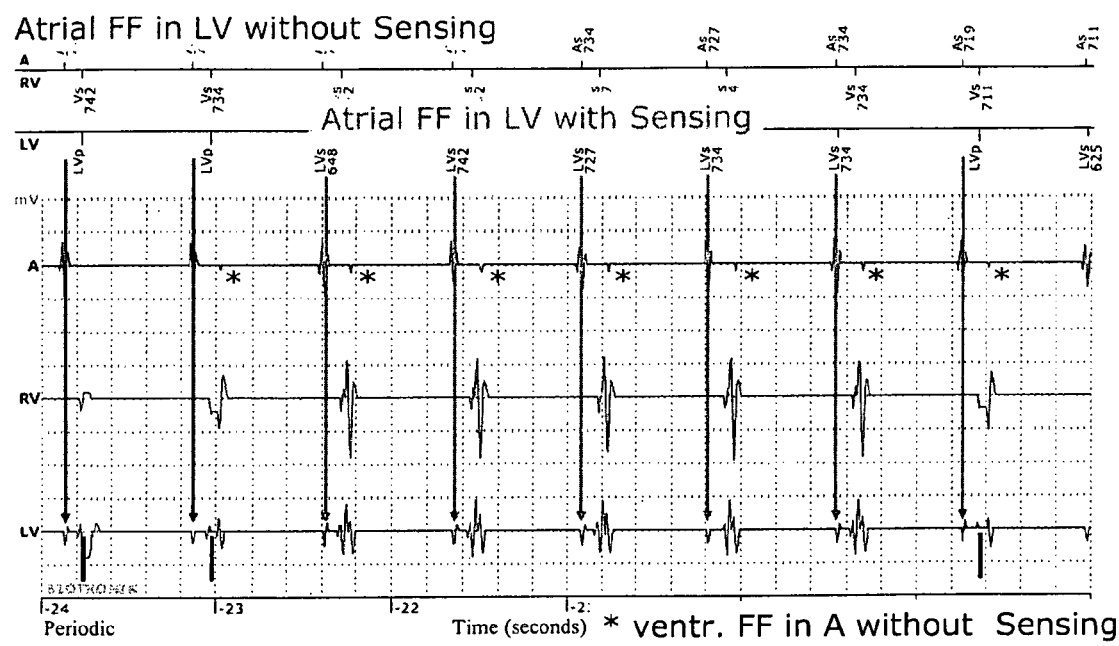

Recommendation:

| - Checking the LV probe position<br>- If nessecary, LV-T wave protection may have to be shut down or the sensitivity in the LV channel may have to be reduced |
|---|

Fig. 8

ECG ANALYZING DEVICE

FIELD OF THE INVENTION

The invention generally relates to a device for processing electrocardiogram signals and marker signals.

BACKGROUND OF THE INVENTION

Implants such as implantable heart pacemakers, ICDs or monitoring devices, which record intracardiac electrocardiograms and obtain marker signals, are essentially known. Intracardiac electrocardiograms (IEGM) are typically in the form of a chronological series of values representing a time-scanned, originally analog signal. Such an electrocardiogram has various typical and periodically recurring signal features representing cardiac events such as contractions of the right or left ventricle, or contractions of the right or left atrium. Signal features representing contractions of the right or left atrium are typically denoted as P waves, while signal features associated with contraction of the ventricle are reflected in a so-called R wave. On the basis of such an electrocardiogram, the implant generates marker signals, which mark the chronological occurrence of detected cardiac events by the fact that the implant detects P waves and R waves, e.g., through a suitable comparison of threshold values. To do so, an intraatrial cardiogram is typically sent to an atrial sensing unit of the implant; the intraatrial electrocardiogram signals thereby picked up are constantly compared to a threshold value; and a marker signal reflecting an atrial event, i.e., contraction of the atrium, is generated when the threshold value is exceeded. Similarly, an intraventricular electrocardiogram is regularly compared with a threshold value by a ventricular sensing unit, and when this threshold value is exceeded, a ventricular marker signal is generated, marking the contraction of the corresponding ventricle. Other typical marker signals contain information about the evaluation and reaction (e.g., treatment) of the implant.

The background is that the contraction of an atrium or a ventricle is associated with depolarization of the respective myocardium (heart muscle tissue), leading to detectable potentials that can be picked up by intraatrial or intraventricular electrodes and ultimately lead to the corresponding signals in the intraatrial and intraventricular electrogram.

Via a corresponding interface for wireless data transmission, such implants are capable of transmitting recorded electrograms by telemetry in the form of electrocardiogram signals as well as marker signals derived from the electrocardiograms to an external device.

SUMMARY OF THE INVENTION

The invention relates to an analyzer device for analyzing/processing electrocardiogram signals and marker signals which is provided intracardially, e.g., with the help of a medical implant such as a heart pacemaker or an implantable cardioverter defibrillator (ICD) or an implantable monitoring device. Such implants usually also generate marker signals. The analyzer device is preferably located outside of the implant, but in principle it may also be part of an implant.

To receive electrocardiogram signals and marker signals from an implant, the analyzer device has an input interface. This input interface is connected to an analyzer unit, which processes the electrocardiogram signals and marker signals. An output interface for output of data representing an analytical report and suitable for being displayed by a playback unit, e.g., a display screen or a printer is in turn connected to the analyzer unit.

In a preferred scenario, the analyzer device is part of a central service center which is typically capable of receiving and processing electrocardiogram signals, marker data, and implant data from an implant via an external device that is situated in proximity to the respective patient and serves as an intermediate sender/transmitter for the signals/data. A central service center readily makes available the resources required for processing so that such resources need not be kept on hand in the implant. However, as technology advances, it is also conceivable to integrate the analyzer device into an implant.

An object of the invention is to create a analyzer device which will support a physician in providing care for a patient. Such devices are fundamentally known. The invention attempts to facilitate the physician's work, and thereby also improve patient care.

In the analyzer device, the analyzer unit is designed to analyze received electrocardiogram signals and marker signals together in such a way that the analyzer unit detects relevant particular features on the basis of predefined criteria, then assigns a priority to the particular features thereby detected, and finally generates an analytical report containing at least a list of the particular features detected.

The particular features to be detected are preferably of a technical nature pertaining to the detection, e.g., features indicating electrode breakage, features indicating oversensing (i.e., indicating that too many events have been detected in a given electrocardiogram), features indicating far-field detection of events in another chamber of the heart or the like. Since the analyzer device automatically detects such particular features and generates an analytical report that is easy for the physician to understand, the device facilitates prompt detection of possible problems by the physician and the implementation of corresponding countermeasures. The analytical report provided by the invention preferably contains a respective electrocardiogram signal section and/or marker signal section representing these particular features in a graphic reproduction, allowing the physician to see an image of the particular event himself on the basis of the basic signals. Since the particular signal sections are emphasized graphically in the analytical report, the doctor knows at first glance which signal sections he may need to examine more closely. Since the analytical report also contains a listing of the detected feature, the physician also knows which actual or presumed feature the analyzer device has automatically detected.

The analyzer device is preferably configurable by a physician in that the device has an input interface which is connected to the analyzer unit, and is designed in combination with the analyzer unit to receive user specifications that influence operation of the analyzer unit in processing the electrocardiogram signals and marker signals. Such user specifications may consist, for example, of the physician selecting features desired for detection from a catalog of particular features that can be detected by the device. The analyzer device (and in particular the analyzer unit) may activate or deactivate certain subunits (e.g., submodules of the analyzer unit) corresponding to the selection. If certain criteria are to apply to detection of a particular feature, these may be set by the physician through corresponding user specifications.

As already indicated, the analyzer unit is preferably designed to detect different types of particular features independently of one another, and it has corresponding subunits and/or submodules addressed to these features.

As an example, an analyzer unit may include a noise detector as a subunit/submodule, with the noise detector being designed to detect sections containing noise beyond a predefined threshold in an electrocardiogram signal. The noise detector can thereby detect a high noise level in the electrocardiogram signals. The threshold above which such noise is detected may be adjustable by the physician via the input interface.

Additionally or alternatively, the analyzer unit may have an artifact detector as a subunit/submodule, designed to detect signal sections in an electrocardiogram signal containing artifacts (e.g., polarization artifacts). Polarization artifacts may be recorded in an electrocardiogram signal following the delivery of a stimulation pulse or defibrillation shock. Such a pulse or shock results in polarization of a boundary layer around an electrode that picks up signals so that the electrode picks up potentials that are not traceable back to depolarization of the myocardium, but instead are artifacts.

Similarly, the analyzer unit may have an oversensing classification unit as a subunit/submodule, which is designed to detect sections having signal features indicative of oversensing in an electrocardiogram signal.

To this end, the analyzer unit preferably has its own event detector as a subunit/submodule that detects events such as atrial depolarization or ventricular depolarization in the received electrocardiogram signals. The event detector is preferably designed to process separate electrocardiogram signals for the atrium and the ventricle in combination with one another to be able, in detection of atrial events in an interatrial electrocardiogram signal, to detect such signal deflections which might be attributable to far-field detection of ventricular events. The respective event detector may fundamentally be designed like a sensing unit within the implant, i.e., events are detected by comparison with a suitable threshold value. The event detector in the analyzer device may have a somewhat more complex design than a sensing unit in an implant.

For example, the event detector may also have or be connected to a morphology classification unit that detects the signal sections characteristic of polarization of the respective myocardium by signal shape analysis, i.e., not by simple threshold value comparison but instead by a more extensive analysis (for example, by analysis of the sequence and polarity of deflections, etc.).

If the analyzer unit of the analyzer device has automatically detected atrial and ventricular events in this way, the latter may be compared with the received marker signals by the oversensing classification unit. If it is found thereby that the analyzer unit of the inventive device has detected far fewer events for a signal section than the number of corresponding marker events in the corresponding marker signal, then this means that the implant generating the marker signals may have detected too many presumed events. This is a case of an oversensing error, because the detection threshold for the respective sensing unit of the implant has not been optimally adjusted.

It is advantageous if the analyzer unit has a marker correlator as a subunit/submodule, wherein the marker correlator is designed to determine chronological correlations between cardiac events detected by the analyzer unit and corresponding markers in the respective marker signals. If this correlation analysis yields a correspondence that is too high, this is a sign that oversensing is occurring. Greater deviation in the received marker signals from the events detected by the analyzer unit is a sign of possible oversensing or undersensing, for example, an improperly adapted detection threshold of a sensing unit of the implant.

The device also preferably has an evaluation unit as a subunit which is connected to the analyzer unit or is part thereof and is designed to evaluate particular features detected by the analyzer unit on the basis of given criteria with regard to their importance, such that particular features that are critical for the patient are evaluated differently than particular features that are not critical for the patient. For example, the evaluation may be according to three values, e.g., a distinction is made between highly critical particular features, moderately critical particular features and less critical particular features.

In this context, the analyzer unit is preferably designed to add a respective analytical report to an evaluation generated by the evaluation unit, i.e., to add, for example, the comments "very critical" or "less critical" or "not critical" in plain text. However, the evaluations may also be added to the analytical report in graphic form, e.g., by adding fields of the analytical report in one color, e.g., red for especially critical particular features, yellow for moderately critical particular features and white for the absence of critical features and moderately critical particular features.

In addition, it is advantageous if the analyzer device has a recommendation unit as a subunit, which is connected to the analyzer unit and is designed to generate an action recommendation for the physician on the basis of the particular features detected in the analyzer unit. In the case of oversensing or undersensing, the action recommendation might be in the direction of raising or lowering the detection threshold of the respective sensing unit, for example. In the case of detection of an electrode breakage, the recommendation might be to replace the stimulation electrode.

To create a respective analytical report from the data obtained previously by the analyzer unit, a report generator is preferably provided, which may optionally be configurable.

The list of the particular features detected is preferably supplemented by prioritization and/or reproduction of an electrocardiogram signal section and/or a marker signal section in a graphic reproduction, optionally with marking of the signal sections representing the particular feature and naming of the particular feature.

Additional preferred versions of the invention involve different combinations of the features described below.

BRIEF DESCRIPTION OF THE DRAWINGS

The invention will now be explained in greater detail on the basis of an exemplary version with reference to the figures, in which:

FIG. 8: shows a fourth example of an analytical report.

DETAILED DESCRIPTION OF EXEMPLARY VERSIONS OF THE INVENTION

Figure 1:
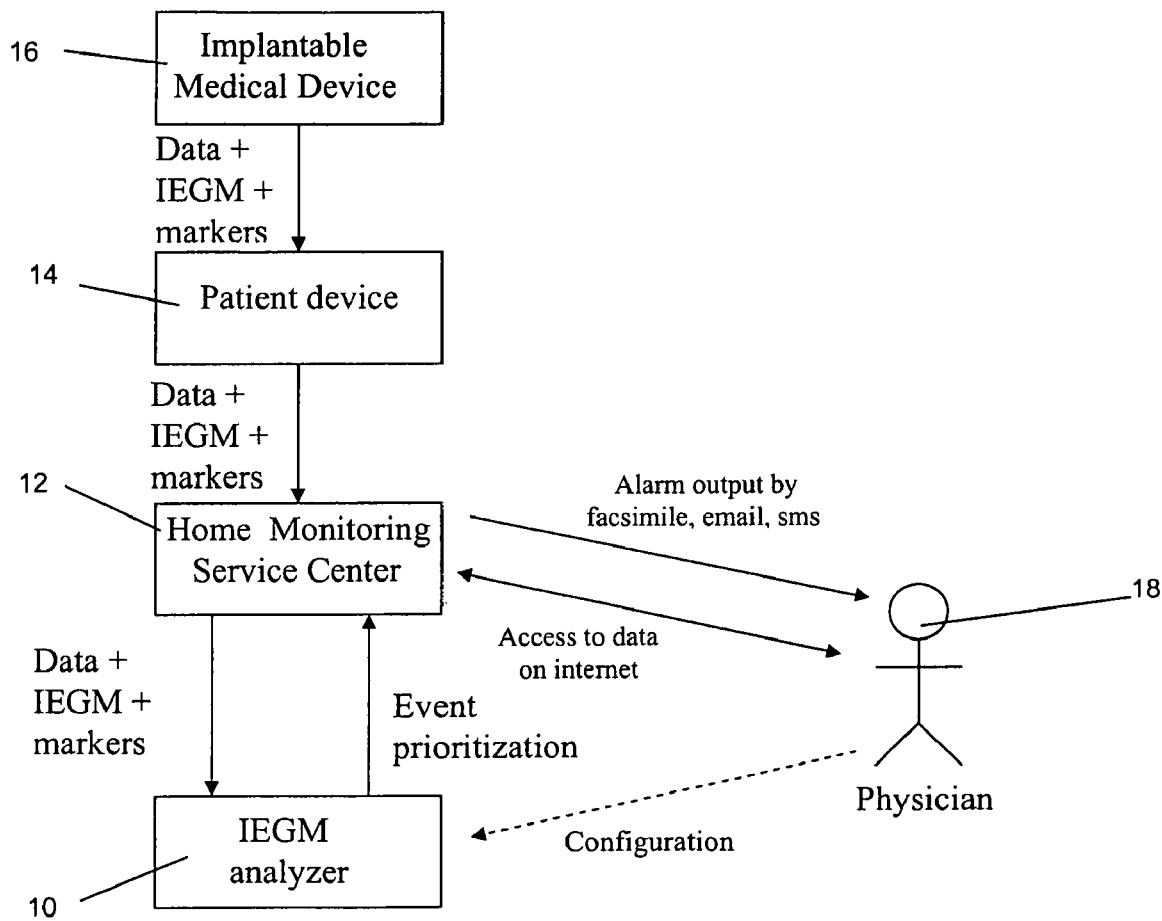
FIG. 1: shows an overview of a system for patient care using a cardiac analyzer device exemplifying the invention.

The system illustrated in FIG. 1 has an electrocardiogram analyzer device 10 as part of a central service center 12, which is connected at least temporarily to an implantable medical device 16 (heart pacemaker, ICD or implantable monitoring device) via an intermediate patient device 14. In this way, the central service center 12 is capable of receiving electrocardiogram signals and marker signals provided in an essentially known manner by the implantable medical device 16. These signals may include, for example, an intraatrial electrocardiogram signal and an intraventricular electrocardiogram signal as well as a marker signal with individual markers for atrial and ventricular events, said signals being obtained by corresponding sensing units of the implantable medical device 16 by internal analysis of the intracardiac electrocardiograms. As already explained previously, this is typically done by comparing a respective intracardiac electrocardiogram signal with corresponding detection thresholds, where the detection threshold for detection of atrial events from an intraatrial electrocardiogram is usually different from the detection threshold for detection of ventricular events in an intraventricular electrocardiogram.

A physician 18 typically has access to the electrocardiogram signals and marker signals received on the part of the implantable medical device 16 via the central service center 12. This access may be accomplished via the Internet, for example, in which case the central service center 12 is typically designed to automatically alert the physician by email, fax or SMS, or other forms of messaging.

Figure 2:
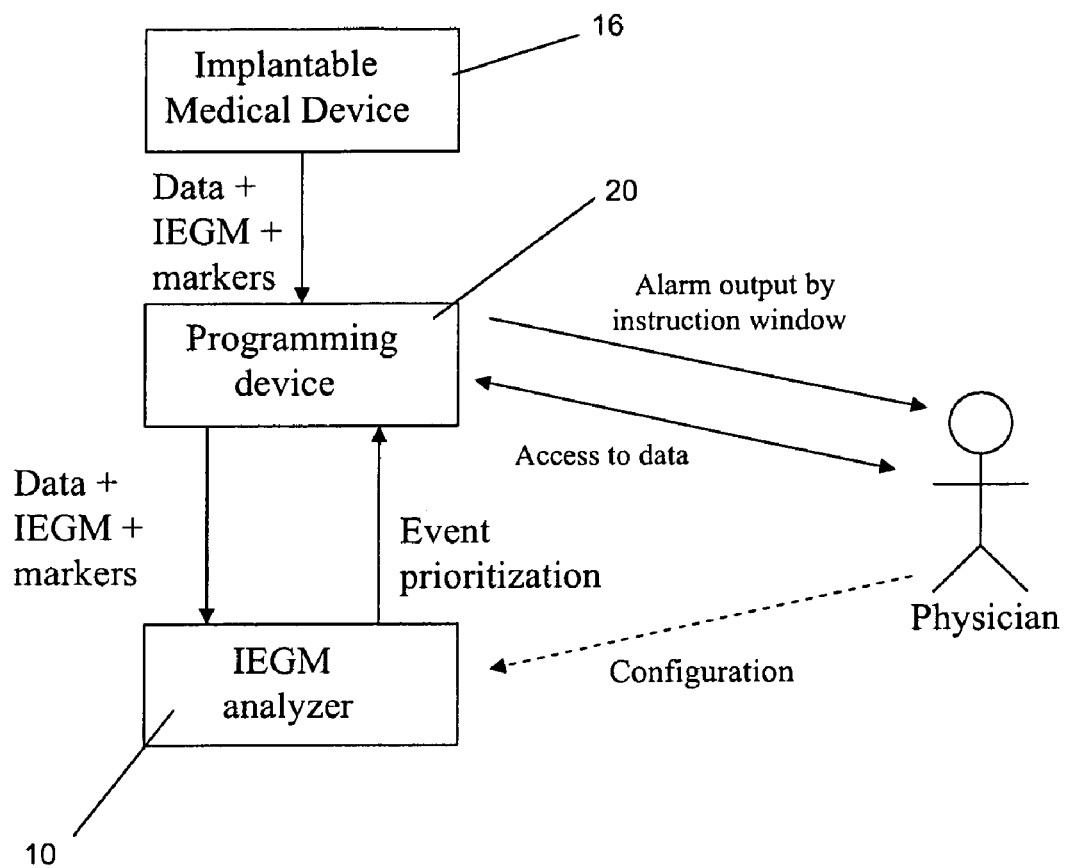
FIG. 2: shows an alternative system with an electrocardiogram analyzer device exemplifying the invention.

FIG. 2 shows that the inventive electrocardiogram analyzer device 10 may also be part of a programming device 20 which a physician uses in a visit for readout of data stored in an implantable medical device 16. In this case the programming device 20 is situated near the medical device 16, so the transmission of the corresponding electrocardiogram signals and marker signals takes place directly from the implantable medical device 16 to the programming device 20 so that these signals are directly available to the physician 18. A programming device 20 typically has a graphic display which also allows graphic reproduction of electrocardiogram signal sections in addition to text. Furthermore, a programming device 20 typically also has an input unit which enables the physician 18 to make entries for controlling the programming device and in particular also for controlling the electrocardiogram analyzer device 10.

Figure 3:
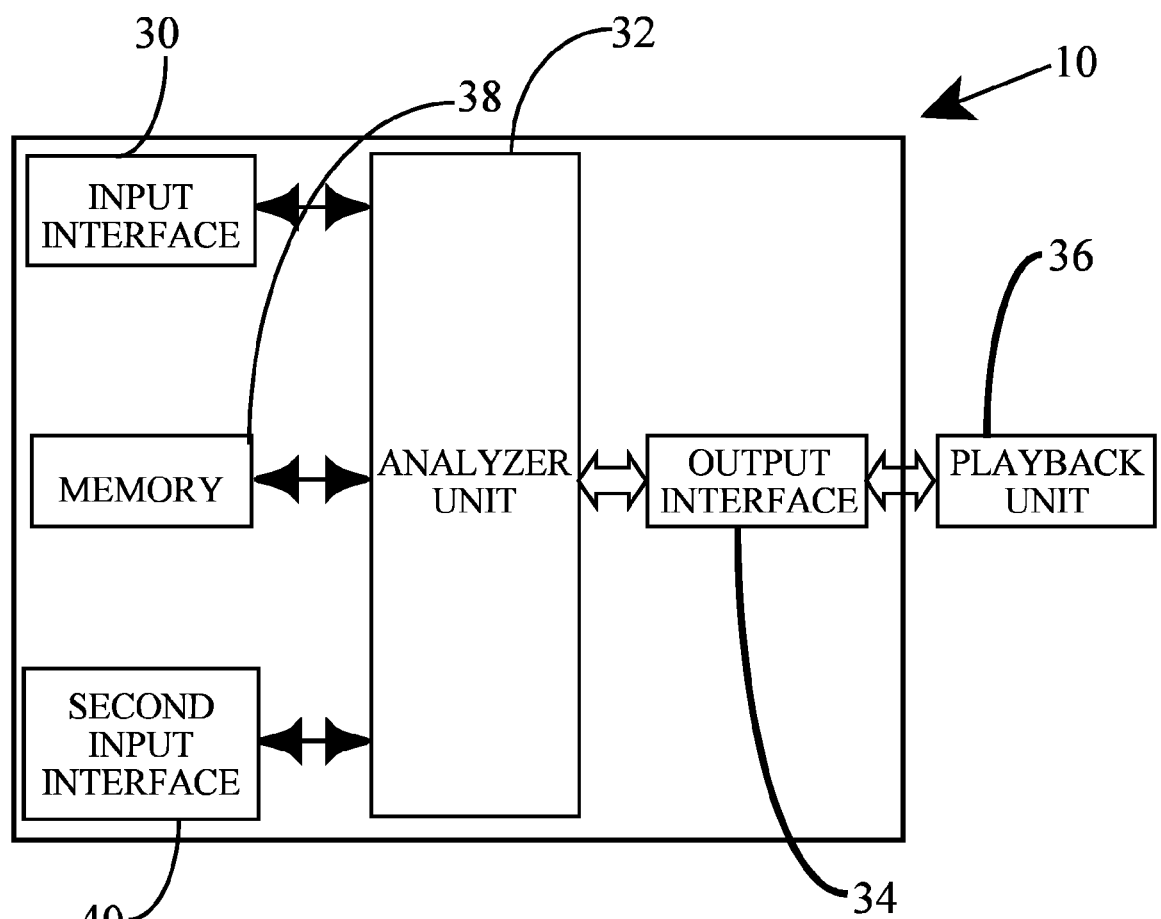
FIG. 3: shows a schematic diagram of an electrocardiogram analyzer device exemplifying the invention.

FIG. 3 shows the electrocardiogram analyzer device 10 from FIG. 1 and FIG. 2 in greater detail.

The device 10 has an input interface 30 for receiving electrocardiogram signals and marker signals which are generated by an implantable medical device 16. An analyzer unit 32 designed for processing the electrocardiogram signals and maker signals in the manner described in greater detail below is connected to the input interface 30. An output interface 34 designed for output of data (e.g., representing an analytical report) is connected to the analyzer unit 32, and also to a playback unit 36 (e.g., a display screen or a printer). Furthermore, the analyzer unit 32 is also connected to a memory 38. An input interface 40 is also connected to the analyzer unit 32 and allows the analyzer unit to be connected to an input device such as a keyboard or the like, which may be part of the device 10.

Figure 4:
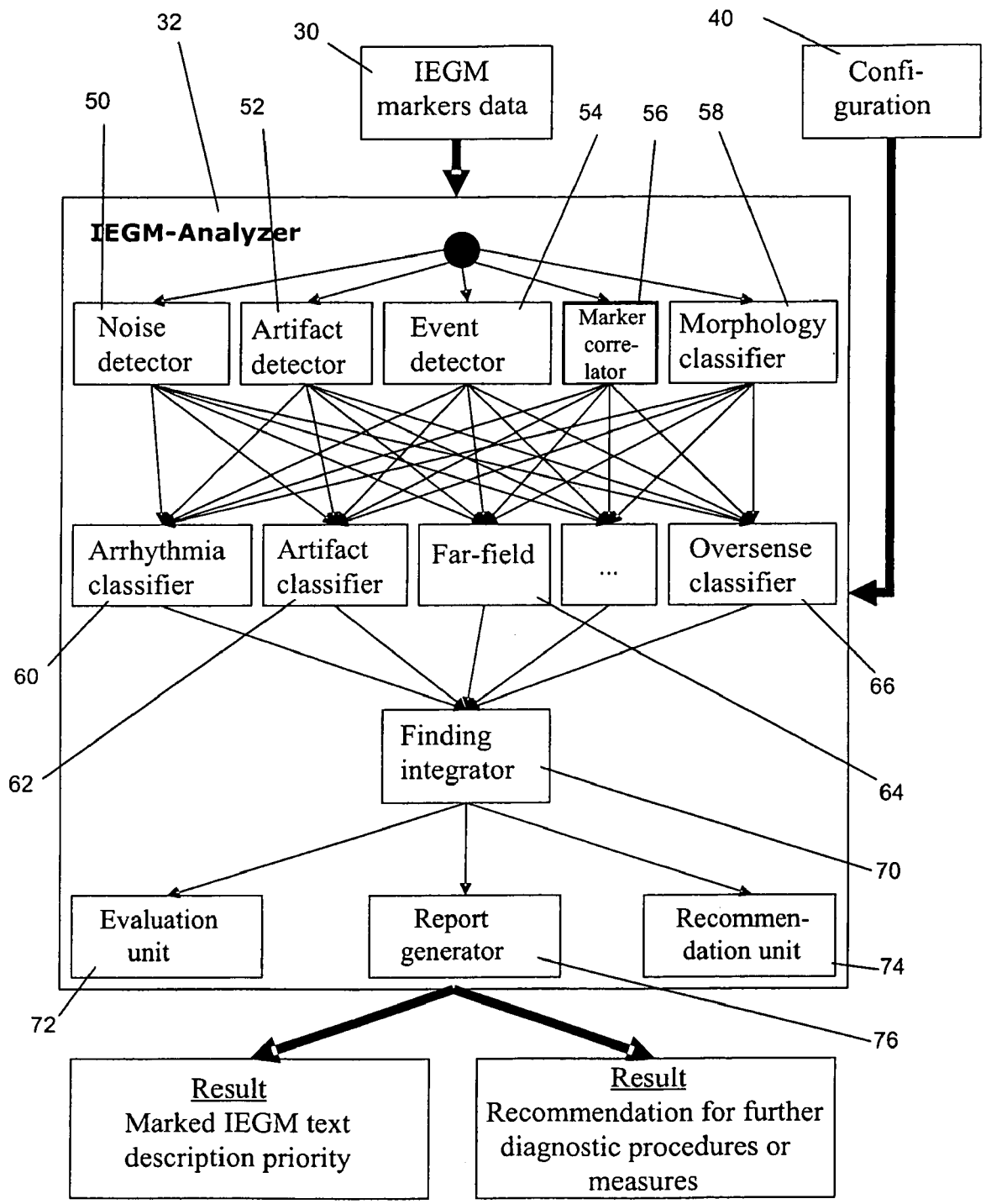
FIG. 4: shows a diagram of the analyzer unit of the electrocardiogram analyzer device.
Figure 5:
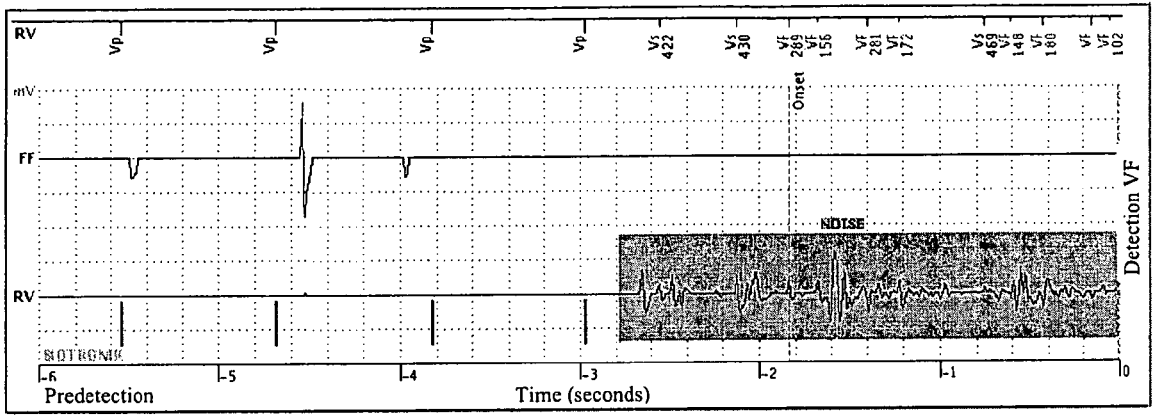
FIG. 5: shows an example of an analytical report generated by the electrocardiogram analyzer device of FIG. 3.
Figure 6:
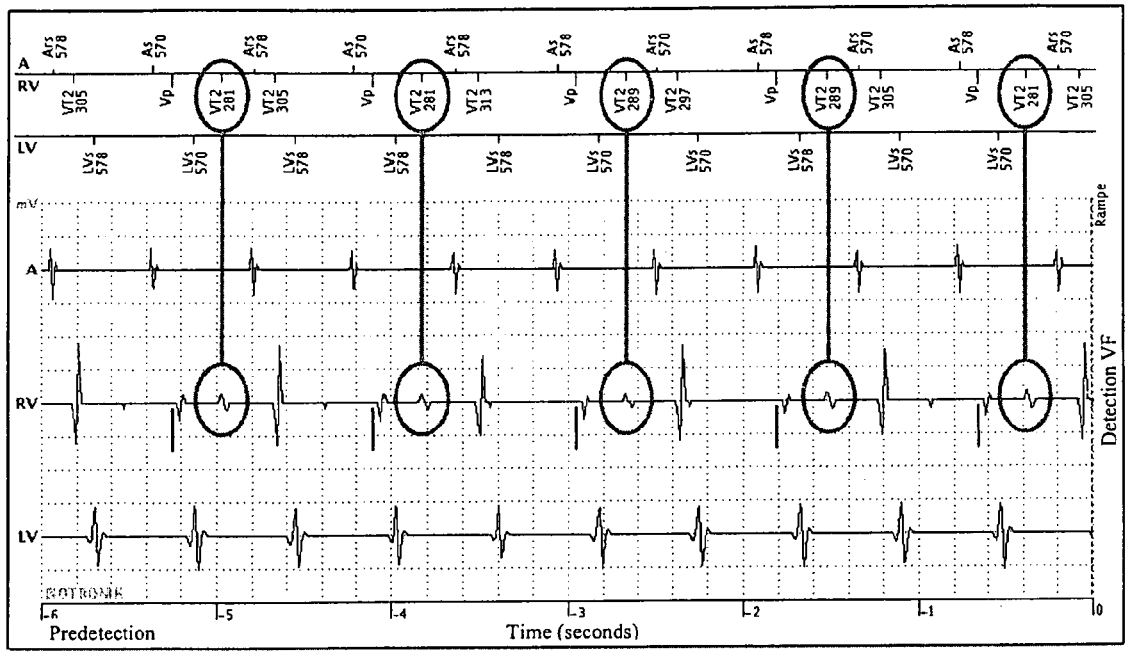
FIG. 6: shows a different analytical report.
Figure 7:
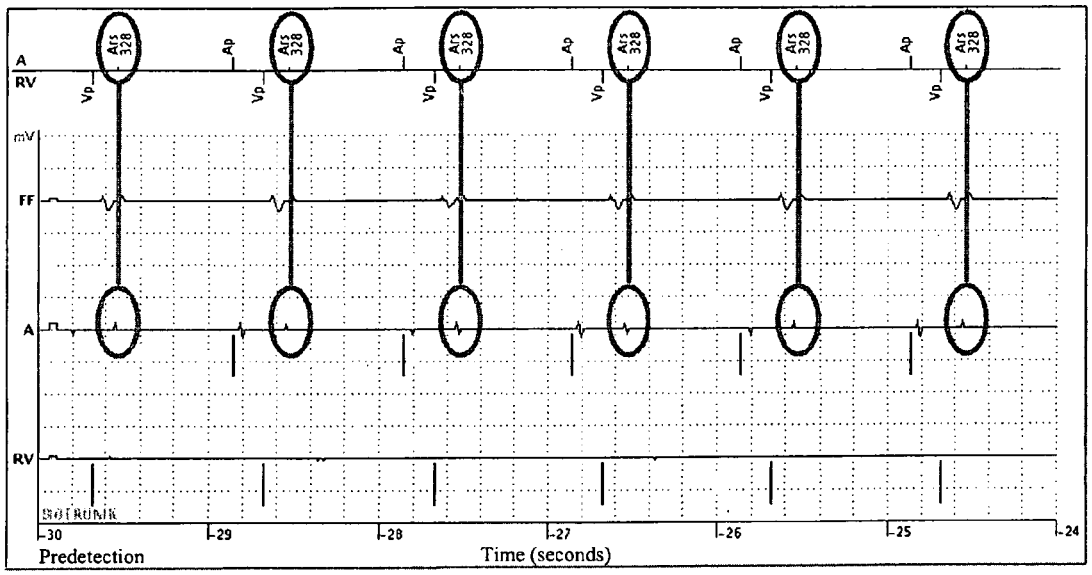
FIG. 7: shows a third analytical report.

FIG. 4 shows a few components of the device 10 in a detailed diagram. In particular, the analyzer unit 32 is shown in greater detail and is connected at the input to the input interface 30 and the (additional) input interface 40. The analyzer unit 32 receives the electrocardiogram signals and marker signals to be processed via the input interface 30, and control commands for configuration of the analyzer unit 32 can be input into the analyzer unit 32 via the input interface 40.

The electrocardiogram signals and marker signals received via the input interface 30 are sent to various subunits (or submodules) of the analyzer unit 32, depending on the configuration. A first category of subunits pertains to the direct signal processing, while a second category of subunits is used for the actual detection of particular features based on the processed signals.

The subunits of the first category include a noise detector 50, an artifact detector 52, an event detector 54, a marker correlator 56 and a morphology classifier 58. Additional signal processing units, or signal processing units other than these, may also or alternatively be provided.

While not immediately shown in the diagram of FIG. 4, the marker correlator 56, the event detector 54 and the morphology classifier 58 may be interconnected, so that the event detector 54 is also able to process output signals of the morphology classifier 58 in particular, and the marker detector 56 can also process output signals of the event detector 54.

The noise detector 50 is designed to detect how high is the noise component of an electrocardiogram signal received via the input interface 30.

The artifact detector 52 is designed to detect possible artifacts in the electrocardiogram signal and in doing so may cooperate with the morphology classifier 58, for example.

The event detector 54 is designed for detecting events, i.e., signals, in the electrocardiogram signal, such that the signals indicate a contraction of the respective ventricle or atrium. As indicated before, multiple event detectors may also be provided, in particular when the analyzer unit 32 receives not just one single electrocardiogram signal but, for example, also receives two or three electrocardiogram signals that were picked up separately in the right atrium, the right ventricle and/or the left ventricle of a heart.

The respective event detector 54 may rely on signals generated by the morphology classifier 58. For example, the morphology classifier 58 may be designed to detect and differentiate artifacts, far-field events or true cardiac events in the respective heart chamber on the basis of the signal morphology.

The event detector 54 performs an independent analysis of the received electrocardiogram signals, and in this way generates marker signals generated in the analyzer unit 32 which can then be compared with the marker signals received via the input interface 30. This may be accomplished by the marker correlator 56. Ideally, the marker signals generated in the analyzer unit 32 correspond to the marker signals received from the input interface 30. This would mean that the corresponding sensing units of the implant 16, which usually operate differently, and the event detector or detectors 54 of the analyzer unit 32 supply results that correspond to one another. However, if the marker signals received via the input interface 30 contain significantly more event markers than the marker signals generated by the event detector 54, this is a sign that the corresponding sensing unit of the implant 16 might perhaps be detecting too many events, which may be a result of oversensing, for example. Oversensing occurs when a sensing unit of the implant performs an event detection on the basis of a threshold value comparison of an intracardiac electrocardiogram with a detection threshold, and the detection threshold is set so low that original cardiac events are detected, but also other signal deflections are falsely detected as cardiac events. Oversensing is then traceable back to an improperly selected detection threshold for the respective sensing unit of the implant, for example.

Conversely, the marker signal received via the input interface 30 may contain far fewer event markers than those detected by the event detector 54. This may be an indication of undersensing, i.e., an indication that the detection threshold of the respective sensing unit of the implant 16 has been set too high, so that not all events are reliably detected in the respective intracardiac electrocardiogram signal because some lead to deflections of the electrocardiogram signal that might not be high enough.

A second category of subunits and/or submodules of the analyzer unit 32 is a series of classification units, each of which is designed to detect certain particular features in the received electrocardiogram signals or marker signals. Such subunits may include, for example, an arrhythmia classifier 60, an artifact classifier 62, a far-field classifier 64 and an oversense classifier 66. Additional classifiers may also be provided. As indicated in FIG. 4, all of these second category classifiers may be linked to subunits of the first category (discussed above) to be able to use the output signals of different subunits of the first category for classification of particular features in the electrocardiogram signal or the marker signal.

The particular features detected in this way are sent to a finding integrator 70 which cooperates with an evaluation unit 72 and a recommendation unit 74 as well as with a report generator 76.

The evaluation unit 72 is designed to evaluate the output signals of the subunits of the second category with regard to the importance of a possible particular feature. Particular features indicating serious disturbances receive an evaluation corresponding to a high priority, whereas particular features indicating a less serious disturbance receive an evaluation indicating a moderate or low priority.

The recommendation unit 74 links a recommendation to the particular features detected. In the case of undersensing, for example, the recommendation may be to lower the detection threshold of the respective sensing unit of the implant 16, or in the case of detection of an electrode breakage, this may be a recommendation to replace the electrode line.

Finally, the results of the finding integrator 70 and the evaluation unit 72 and the recommendation unit 74 are sent to the analytical report generator 76, which generates an analytical report containing a graphic representation of the electrocardiogram signal section or marker signal section affected by a particular feature, and also a naming of the particular feature detected by the analyzer unit 32. In addition, the analytical report generated by the analytical report generator 76 contains an evaluation of the respective particular feature detected in the form of a notation, e.g., "high priority," "moderate priority" or "low priority." Finally, the analytical report contains a respective handling recommendation for the physician as generated by the recommendation unit 74.

The analytical report generated in this way is finally available at the output interface 34 (FIG. 3) for forwarding to a display device 36, e.g., a display screen or another reproduction device, e.g., a printer. It is self-evident that this display device may also be set up at a great distance from the analyzer unit 32, e.g., may be connected to the analyzer unit 32 via the Internet.

FIGS. 5 to 8 show various exemplary analytical reports generated by the analytical report generator 76 on the basis of the analysis of the electrocardiogram signals and marker signals by the analyzer unit 32. It can be seen here that each analytical report first contains a reference to the priority of the detected particular feature as determined by the evaluation unit 72. This is followed by a description of the detected particular feature. Next there is a representation of the respective signal section affected in a graphic plot. Finally, each analytical report also contains a recommendation for the respective treating physician.

In this way, the analyzer unit 12 makes it much easier for the physician to detect particular features and optionally to perform necessary actions.

What is claimed is:

1. A device (10) for processing electrocardiogram signals and marker signals including:
    a. an input interface (30) receiving electrocardiogram signals and marker signals detected by an implantable medical device;
    b. an analyzer unit (32) connected to the input interface (30), the analyzer unit (32):
        (1) processing the electrocardiogram signals and marker signals,
        (2) detecting particular features in one or more of the electrocardiogram signals and marker signals on the basis of predefined detection criteria,
        (3) assigning priority rankings to detected particular features,
        (4) generating analyzer marker signals marking at least some of the detected particular features of the electrocardiogram signals, and
        (5) comparing the input marker signals and analyzer marker signals for differences; and
    c. an output interface (34) connected to the analyzer unit (32), the output interface (34) outputting data representing an analytical report, the analytical report containing at least a listing of the detected particular features.

2. The device of claim 1 further including a second input interface (40) connected to the analyzer unit (32), the second input interface (40) receiving user specifications influencing the processing of the electrocardiogram signals and marker signals by the analyzer unit (32).

3. The device of claim 1 wherein the analyzer unit (32) includes a noise detector (50) detecting sections of the electrocardiogram signals having a noise level beyond a predefined limit value.

4. The device of claim 1 wherein the analyzer unit (32) includes an artifact detector (52) detecting sections of the electrocardiogram signals having polarization or other artifacts.

5. The device of claim 1 wherein the analyzer unit (32) includes an event detector (54) detecting sections of the electrocardiogram signals characteristic of depolarization of the myocardium.

6. The device of claim 5 wherein the event detector (54) is in communication with a morphology classification unit (58) performing signal shape analysis of the electrocardiogram signals.

7. The device of claim 1 wherein:
    a. the input marker signals and analyzer marker signals are compared for differences in timing along the electrocardiogram signals, and
    b. the analyzer unit (32) generates:
        (1) an output indicative of oversensing if the input marker signals are greater in number than the analyzer marker signals, and
        (2) an output indicative of undersensing if the input marker signals are fewer in number than the analyzer marker signals.

8. The device of claim 1 wherein the listing of the detected particular features is supplemented by one or more of:
    a. a graphic reproduction of at least a section of the electrocardiogram signals, b. a graphic reproduction of at least a section of the marker signals, whereupon one or more of the detected particular features are marked.

9. The device of claim 1 wherein the analyzer unit (32) includes a marker correlator (56) determining correlations in time between detected cardiac events and corresponding markers in the marker signals.

10. The device of claim 1 wherein the analyzer unit (32) includes an oversensing classification unit (66) detecting sections of the electrocardiogram signals having characteristics indicative of oversensing.

11. The device of claim 1 further including an evaluation unit (72) in communication with the analyzer unit (32), the evaluation unit (72):
   a. evaluating detected particular features with regard to their importance on the basis of predefined priority ranking criteria, and
   b. assigning the priority rankings to the detected particular features.

12. The device of claim 1 further including a recommendation unit (74) in communication with the analyzer unit (32), the recommendation unit (74) generating a treatment recommendation based on the particular features detected by the analyzer unit (32).

13. A device (10) for processing electrocardiogram signals and marker signals including:
   a. an input interface (30) receiving electrocardiogram signals and marker signals detected by an implantable medical device;
   b. an analyzer unit (32) connected to the input interface (30), the analyzer unit (32):
      (1) including a marker correlator (56) determining correlations in time between detected cardiac events and corresponding markers in the marker signals;
      (2) processing the electrocardiogram signals and marker signals;
      (3) detecting particular features in one or more of the electrocardiogram signals and marker signals on the basis of predefined detection criteria; and
      (4) assigning priority rankings to detected particular features;
   c. an output interface (34) connected to the analyzer unit (32), the output interface (34) outputting data representing an analytical report, the analytical report containing at least a listing of the detected particular features.

14. The device of claim 13 wherein the analyzer unit (32) includes an oversensing classification unit (66) detecting sections of the electrocardiogram signals having characteristics indicative of oversensing.

15. The device of claim 13 further including an evaluation unit (72) in communication with the analyzer unit (32), the evaluation unit (72):
   a. evaluating detected particular features with regard to their importance on the basis of predefined priority ranking criteria, and
   b. assigning the priority rankings to the detected particular features.

16. The device of claim 13 further including a recommendation unit (74) in communication with the analyzer unit (32), the recommendation unit (74) generating a treatment recommendation based on the particular features detected by the analyzer unit (32).

17. A device (10) for processing electrocardiogram signals and marker signals including:
   a. an input interface (30) receiving electrocardiogram signals and marker signals detected by an implantable medical device;
   b. an analyzer unit (32) connected to the input interface (30), the analyzer unit (32):
      (1) including an oversensing classification unit (66) detecting sections of the electrocardiogram signals having characteristics indicative of oversensing;
      (2) processing the electrocardiogram signals and marker signals;
      (3) detecting particular features in one or more of the electrocardiogram signals and marker signals on the basis of predefined detection criteria; and
      (4) assigning priority rankings to detected particular features;
   c. an output interface (34) connected to the analyzer unit (32), the output interface (34) outputting data representing an analytical report, the analytical report containing at least a listing of the detected particular features.

18. A device (10) for processing electrocardiogram signals and marker signals including:
   a. an input interface (30) receiving electrocardiogram signals and marker signals detected by an implantable medical device;
   b. an analyzer unit (32) connected to the input interface (30), the analyzer unit (32):
      (1) processing the electrocardiogram signals and marker signals, and
      (2) detecting particular features in one or more of the electrocardiogram signals and marker signals on the basis of predefined detection criteria, and
      (3) assigning priority rankings to detected particular features;
   c. an evaluation unit (72) in communication with the analyzer unit (32), the evaluation unit (72):
      (1) evaluating detected particular features with regard to their importance on the basis of predefined priority ranking criteria, and
      (2) assigning the priority rankings to the detected particular features; and
   d. an output interface (34) connected to the analyzer unit (32), the output interface (34) outputting data representing an analytical report, the analytical report containing at least a listing of the detected particular features.

19. The device of claim 18 wherein the analyzer unit (32) includes an oversensing classification unit (66) detecting sections of the electrocardiogram signals having characteristics indicative of oversensing.

20. The device of claim 18 further including a recommendation unit (74) in communication with the analyzer unit (32), the recommendation unit (74) generating a treatment recommendation based on the particular features detected by the analyzer unit (32).

21. A device (10) for processing electrocardiogram signals and marker signals including:
   a. an input interface (30) in communication with an implantable medical device, the input interface (30) receiving
      (1) electrocardiogram signals, and
      (2) input marker signals marking features of the electrocardiogram signals, from the implantable medical device;
   b. an analyzer unit (32) receiving the electrocardiogram signals and input marker signals from the input interface (30), the analyzer unit (32):
      (1) applying predefined detection criteria to one or more of the electrocardiogram signals and input marker signals, thereby identifying particular features in one or more of the electrocardiogram signals and input marker signals which meet the predefined detection criteria;

(2) applying predefined priority ranking criteria to the identified particular features, thereby assigning priority rankings to the identified particular features;

(3) generating analyzer marker signals marking particular features identified within the electrocardiogram signals;

(4) comparing the input marker signals and analyzer marker signals for differences;

(5) generating an output report containing:
  i. at least a listing of the identified particular features having the highest priority rankings,
  ii. an indication of oversensing if the input marker signals are greater in number than the analyzer marker signals, and
  iii. an indication of undersensing if the input marker signals are fewer in number than the analyzer marker signals.

22. A device (10) for processing electrocardiogram signals and marker signals including:
  a. an input interface (30) receiving electrocardiogram signals and marker signals detected by an implantable medical device;
  b. an analyzer unit (32) connected to the input interface (30), the analyzer unit (32):
    (1) processing the electrocardiogram signals and marker signals, and
    (2) detecting particular features in one or more of the electrocardiogram signals and marker signals on the basis of predefined detection criteria, and
    (3) assigning priority rankings to detected particular features;
  c. a recommendation unit (74) in communication with the analyzer unit (32), the recommendation unit (74) generating a treatment recommendation based on the particular features detected by the analyzer unit (32);
  d. an output interface (34) connected to the analyzer unit (32), the output interface (34) outputting data representing an analytical report, the analytical report containing at least a listing of the detected particular features.

23. The device of claim 21 further including a recommendation unit (74) in communication with the analyzer unit (32), the recommendation unit (74) generating a treatment recommendation based on the particular features detected by the analyzer unit (32).

24. The device of claim 23 wherein the listing of the detected particular features is supplemented by one or more of:
  a. a graphic reproduction of at least a section of the electrocardiogram signals,
  b. a graphic reproduction of at least a section of the marker signals, whereupon one or more of the detected particular features are marked.

25. A device (10) for processing electrocardiogram signals and marker signals including:
  a. an input interface (30) in communication with an implantable medical device, the input interface (30) receiving
    (1) electrocardiogram signals, and
    (2) input marker signals marking features of the electrocardiogram signals, from the implantable medical device;
  b. an analyzer unit (32) receiving the electrocardiogram signals and input marker signals from the input interface (30), the analyzer unit (32):
    (1) applying predefined detection criteria to one or more of the electrocardiogram signals and input marker signals, thereby particular features in one or more of the electrocardiogram signals and input marker signals which meet the predefined detection criteria;
    (2) applying predefined priority ranking criteria to the identified particular features, thereby assigning priority rankings to the identified particular features;
    (3) generating a treatment recommendation corresponding to one or more of the identified particular features having the highest priority rankings, and
    (3) generating an output report containing:
      i. at least a listing of the identified particular features having the highest priority rankings, and
      ii. the generated treatment recommendation.

26. The device of claim 25 further including a recommendation unit (74) in communication with the analyzer unit (32), the recommendation unit (74) generating a treatment recommendation based on the particular features detected by the analyzer unit (32).

27. The device of claim 25 wherein:
  a. the output report further contains a graphic reproduction of:
    (1) at least some of the electrocardiogram signals,
    (2) at least some of the marker signals,
  b. at least one of the identified particular features having the highest priority rankings is illustrated on the graphic reproduction.

28. A device (10) for processing electrocardiogram signals and marker signals including:
  a. an input interface (30) in communication with an implantable medical device, the input interface (30) receiving
    (1) electrocardiogram signals, and
    (2) input marker signals marking features of the electrocardiogram signals, from the implantable medical device;
  b. an analyzer unit (32) in communication with the input interface (30), the analyzer unit (32):
    (1) detecting particular features in the electrocardiogram signals, and
    (2) generating analyzer marker signals marking the detected particular features of the electrocardiogram signals,
    (3) comparing the input marker signals and analyzer marker signals for differences; and
  c. an output interface (34) connected to the analyzer unit (32), the output interface (34) outputting data representing an analytical report, the analytical report containing at least a listing of some of the detected particular features for which both input marker signals and analyzer marker signals exist.

29. The device (10) of claim 28 wherein the analytical report includes a recommendation regarding adjustment of the implantable medical device if the input marker signals and analyzer marker signals differ in their number and time of occurrence over the electrocardiogram signals.

30. The device (10) of claim 28 wherein:
  a. the input marker signals from the implantable medical device, and
  b. the analyzer marker signals generated by the analyzer unit (32), are generated by different detection algorithms.

* * * * *